(12) United States Patent
Bob et al.

(10) Patent No.: US 7,794,390 B2
(45) Date of Patent: Sep. 14, 2010

(54) ENDOSCOPE HAVING A ROTATABLE DISTAL ENDOSCOPE HEAD

(75) Inventors: Konstantin Bob, Weinheim (DE); Fritz Pauker, Kissing (DE); Thomas Viebach, Pischertshofen (DE)

(73) Assignee: invendo medical GmbH (DE)

( * ) Notice: Subject to any disclaimer, the term of this patent is extended or adjusted under 35 U.S.C. 154(b) by 447 days.

(21) Appl. No.: 11/294,897

(22) Filed: Dec. 6, 2005

(65) Prior Publication Data

US 2006/0167342 A1 Jul. 27, 2006

(30) Foreign Application Priority Data

Dec. 7, 2004 (DE) .................. 10 2004 058 929

(51) Int. Cl.
*A61B 1/00* (2006.01)
(52) U.S. Cl. ........................... 600/137; 600/139
(58) Field of Classification Search .................. 600/131, 600/136, 137, 139, 141, 146; 604/108, 165.04
See application file for complete search history.

(56) References Cited

U.S. PATENT DOCUMENTS

| | | | |
|---|---|---|---|
| 4,215,678 A * | 8/1980 | Heine et al. ............... 600/182 |
| 4,466,444 A * | 8/1984 | Baba ........................ 600/139 |
| 4,577,621 A * | 3/1986 | Patel ........................ 600/114 |
| 4,688,554 A * | 8/1987 | Habib ....................... 600/114 |
| 4,880,011 A * | 11/1989 | Imade et al. .............. 600/462 |
| 4,976,191 A | 12/1990 | Suzumori et al. |
| 5,019,121 A | 5/1991 | Krauter |
| 5,314,408 A * | 5/1994 | Salmon et al. ............. 604/22 |
| 5,396,880 A * | 3/1995 | Kagan et al. .............. 600/109 |
| 7,297,087 B2 * | 11/2007 | Degen et al. .............. 475/347 |
| 2003/0181785 A1 | 9/2003 | Viebach et al. |

FOREIGN PATENT DOCUMENTS

FR 2838325 10/2003

OTHER PUBLICATIONS

Gear Ratio (Reduction Gear), Published by Wikipedia, Retrieved from (http://en.wikipedia.org/wiki/Reduction_gear, on Mar. 18, 2008)-pp. 1-5.*
European Search Report for EP05026722, 3 pages.

* cited by examiner

*Primary Examiner*—Linda C Dvorak
*Assistant Examiner*—Alireza Nia
(74) *Attorney, Agent, or Firm*—Hanley, Flight & Zimmerman, LLC

(57) ABSTRACT

The invention relates to an endoscope comprising an endoscope head which is connected to an endoscope shaft by means of a bendable end piece to form a tubular component. According to the invention, an additional rotary member is inserted between the endoscope shaft and the bendable end piece for rotation of the bendable end piece about the longitudinal axis of the endoscope shaft.

21 Claims, 4 Drawing Sheets

ENDOSCOPE HAVING A ROTATABLE DISTAL ENDOSCOPE HEAD

BACKGROUND OF THE INVENTION

The present invention relates to an endoscope having a rotatable distal end piece according to the preamble of claim 1.

From prior art endoscopes of the present inventor itself are known whose respective distal end piece in the form of a deflecting, as it is called, is bendable to all sides at a narrow bending radius. The deflecting substantially serves for facilitating the inserting operation of the endoscope, for instance, in the intestines of a patient by dynamically adapting the deflecting in accordance with the individual loops of the intestines and, thus, the inserting operation being considerably facilitated and consequently being less painful to the patient.

Usually an endoscope head, as it is called, in which a plurality of means required for an endoscopy is arranged is disposed at the endoscope tip. These means include, inter alia, lighting as well as rinsing means and, of course, a photosensitive element, for example in the form of an optical means, a photosensitive electronic component or a light conductor. The optical means serves for extending the viewing angle so as to be able to view as large an area as possible of the intestinal wall surrounding the endoscope head.

From the foregoing brief description of this complex component it becomes clear that a plurality of technical devices have to be arranged especially at the distal end portion of the endoscope so as to ensure the functioning thereof. On the other hand, there is only a relatively small building space available which forces miniaturization of all parts. These miniaturizations are necessarily limited, however, because from a certain degree of miniaturization the functioning especially of the mechanical parts cannot be ensured any more.

In view of this technical situation, it is necessary to provide an endoscope which fulfills the above-mentioned characteristics of modern endoscopes in which, however, a smaller building space is necessary or, rather, the building space available is exploited in a better way.

SUMMARY OF THE INVENTION

This object is achieved, according to the invention, by an endoscope comprising the features of claim 1. Further advantageous configurations of the invention are the subject matter of the other subclaims.

Accordingly, the basic principle of the invention consists in subdividing the movement apparatus of the above-defined deflecting into a rotational mechanism and a bending mechanism and to arrange both mechanisms at an axial distance from each other. By this principle of the invention the building space which is sufficiently available in the longitudinal direction of the endoscope can be utilized in a better way, whereas the building space which is provided in an axial portion of the endoscope in the radial direction to a restricted extent only need not be completely utilized any more in order to accommodate all necessary means of the endoscope. As a consequence, it is the substantial advantage of this principle of the invention that, by a reduction of the outer radial dimensions permitted in this way, even smaller bending radii can be obtained especially in the area of the distal end portion of the endoscope and, thus, the range of application of the endoscope is enlarged.

To put it more concretely, the deflecting of the endoscope according to the invention includes a bending mechanism preferably in the form of such (individual) bellows which permits a bending movement in substantially (preferably) only one single direction or in only one plane of curvature (two-dimensional). Since a bending movement to all directions is possible only by a plurality of such bending mechanisms preferably in the form of bellows, according to the invention a number of bending mechanisms therefore can be dispensed with. Instead, a rotary member is arranged axially offset (below) with respect to the deflecting by means of which the deflecting can be rotated about the longitudinal axis thereof or the longitudinal axis of the endoscope shaft. In this way, consequently the deflecting can be bent to all directions by the superimposed movements of the bending and rotating mechanism.

Advantageously the rotating member is a coaxial drive such as, for instance, a turbine so that a working passage of the endoscope usually extending in the center of the endoscope shaft can also be guided through the rotary member. Moreover, a sufficient torque can be generated by such a drive so that an alignment against a mechanical resistance inside a body cavity is possible. Finally these drives can be inexpensively manufactured for a disposable instrument.

In order to exploit the relatively high speeds of such a turbine for a most exactly controllable rotation of the deflecting, a reduction gear, preferably also in axial construction mode, is necessary as a rule. For this purpose, substantially gears of high reduction (self-locking) such as the so-called harmonic drive, planetary gear sets or cycloid gears are used. These gears have the essential advantage of being adapted to be arranged coaxially with respect to the turbine, whereby in the gear set through-holes extending quasi necessarily centrally are provided through which the working and supply passages for the endoscope head can be guided.

Moreover, all of the afore-mentioned components can be advantageously manufactured in a cost-effective injection molding technique. Electric lines for components provided in the endoscope head such as, e.g., camera chips, LED etc. which are possibly not guided inside the afore-mentioned through bore can be electrically coupled by means of slip rings.

BRIEF DESCRIPTION OF THE DRAWINGS

Hereinafter the invention will be explained in greater detail by way of a preferred embodiment with reference to the accompanying drawings, in which.

DETAILED DESCRIPTION OF THE PREFERRED EMBODIMENTS

Figure 1:
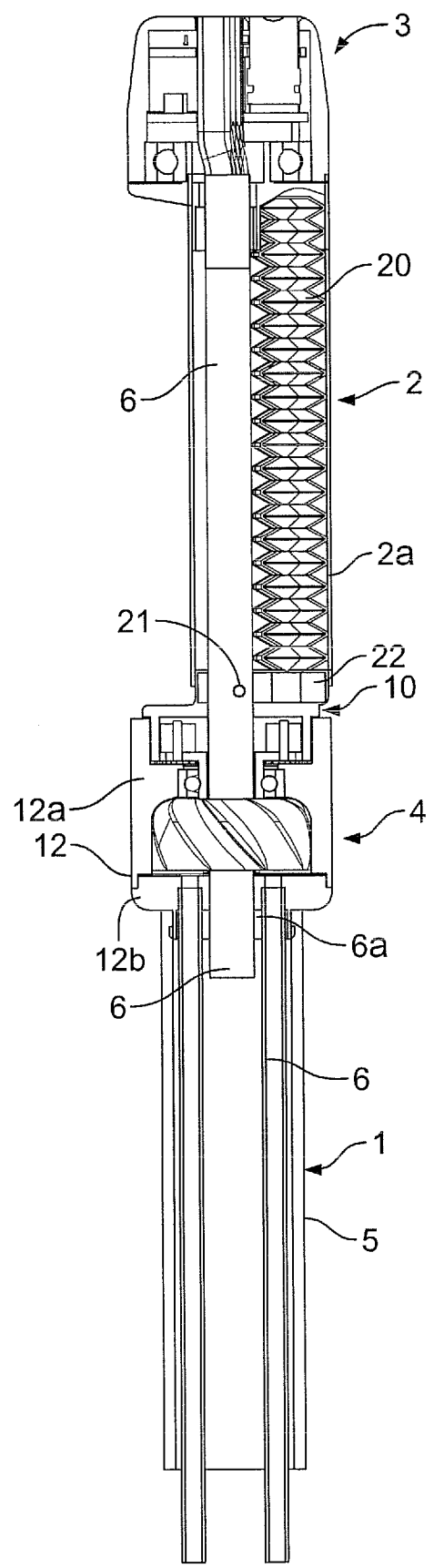
FIG. 1 shows a perspective view of the distal end piece of the endoscope according to the invention.

In accordance with FIG. 1, the endoscope according to the preferred embodiment of this invention comprises an endoscope shaft 1 the distal end piece of which is formed of a bendable operating member (hereinafter referred to as "deflecting") 2, an endoscope head 3 as well as a rotary member 4. The rotary member 4 is disposed between the endoscope shaft 1 and the deflecting 2 and serves for moving the deflecting 2 as well as the axially connected endoscope head 3 by rotation about the longitudinal axis of the deflecting 2 and of the endoscope shaft 1, respectively.

In the present embodiment the endoscope shaft 1 as well as the rotary member 4 are formed as separate components, wherein they are assembled, for instance, by means of a front-side bayonet joint or screwed plug to provide an endoscope. This assembly could also be brought about, of course, by gluing, welding or by a plug-in mechanism, as will be described hereinafter in detail. As an alternative, it is also possible, of course, to integrate the rotary member 4 in the endoscope shaft 1 as a part of the latter for example.

According to FIG. 1, the endoscope shaft 1 has, inter alia, a preferably cylindrical or hose-type outer wall 5 as well as an inner pipe 6 extending coaxially with respect to the outer wall, thereby an area annular in cross-section being formed in which a plurality of working and supply passages, leads and the like are arranged which are not shown and will not be described hereinafter in detail. Thus, the structure of the endoscope shaft 1 substantially corresponds to the shaft structure of already known endoscopes as they are also the subject matter of earlier patent applications of the inventor itself.

To the front face of said endoscope shaft 1 the rotary member 4 is connected as already briefly indicated before. In the present case, the rotary member 4 according to FIG. 2 includes a turbine 7 the driven shaft 9 of which is connected to a reduction gear 10 whose driven shaft 11 in turn is connected in a torque-proof manner to the axially connected deflecting 2.

Moreover, the rotary member 4 includes a housing 12 which in the present case has an outer cylindrical central portion 12a closed by a cover 12b having a pipe connection 12c at its side facing the endoscope shaft 1. It is pointed out that the cover 12b includes a central through-bore through which the inner pipe 6 of the endoscope shaft 1 is guided.

Figure 2:
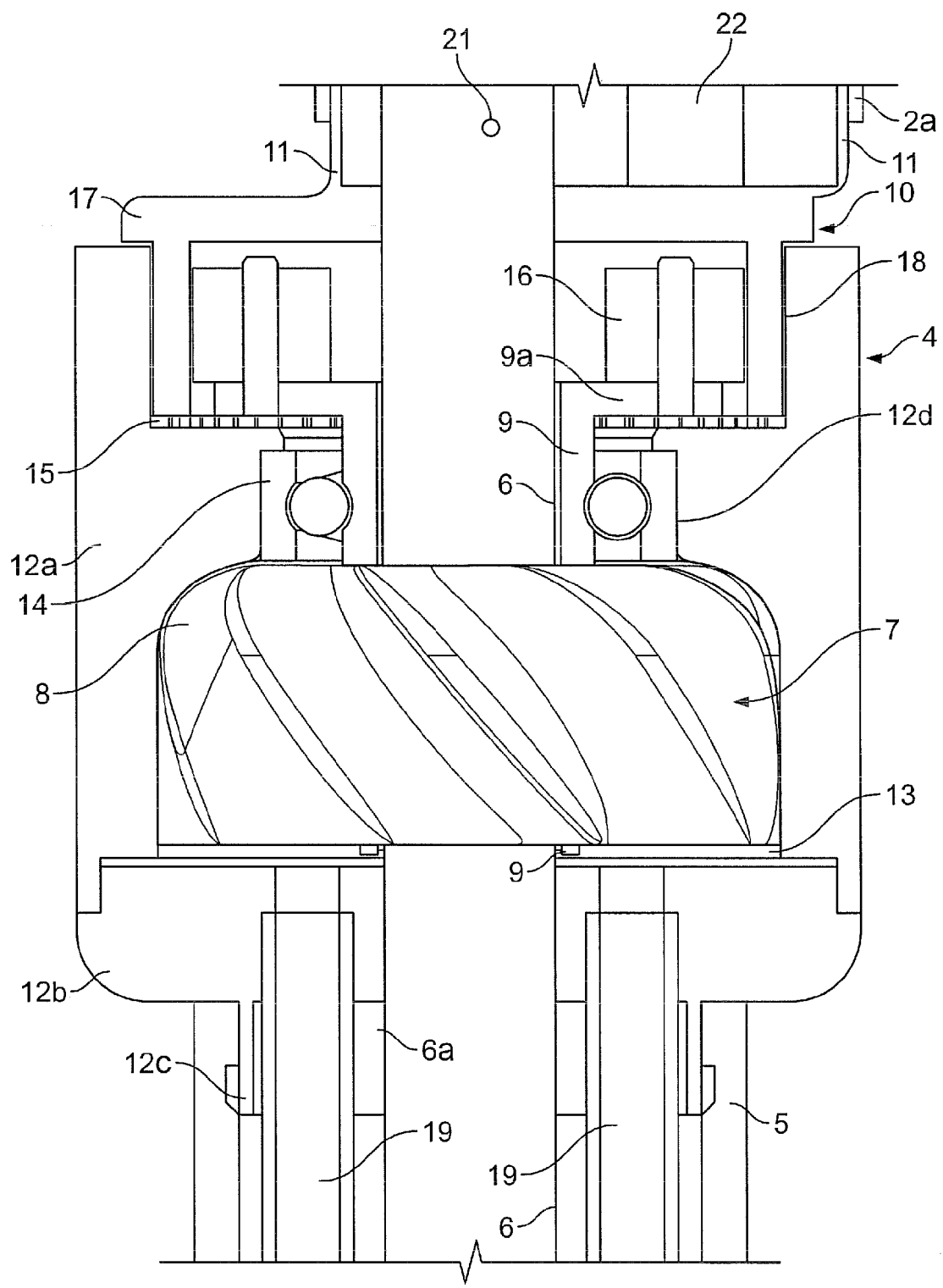
FIG. 2 shows a basic side view of a partial area of the distal end piece of an endoscope according to the invention.

As one can take especially from FIG. 2, the pipe connection 12c forms a pipe frustum extending axially in the direction of the endoscope shaft 1 at the free end of which catch elements are provided in the form of radially outwardly protruding projections, for instance. Said pipe frustum 12c is fixedly anchored in the endoscope shaft 1 by means of the catch elements by the fact that the pipe frustum 12c is indented in the endoscope shaft 1 at the front side, the catch elements thereby interlocking in the shank material. Together with the cover 12b, the cylindrical central portion 12a of the housing 12 forms a receiving chamber 13 for the turbine 7.

In detail the turbine 7 is formed of a turbine wheel 8 as well as a stator which is constituted, in the present case, by the central portion 12a of the housing 12. The turbine wheel 8 is provided with a central bore whose diameter is dimensioned such that a pipe representing an extension of the inner pipe 6 extending in the endoscope shaft 1 can freely pass through (i.e. in a manner rotatable relative to the turbine wheel 8). This extension pipe is preferably inserted in the inner pipe 6 of the endoscope shaft and is sealed by means of a ring seal 6a. As an alternative, said extension pipe can also be the inner pipe 6 of the endoscope shaft 1 itself.

Furthermore, at the turbine wheel 8 a tubular shank surrounding the inner pipe 6 is arranged which extends axially in the direction of the deflecting 2 and on which a roller bearing 14 is seated directly adjacent to the turbine wheel 8. This tubular shank forms the driven shaft 9 or the rotor of the turbine 7. The roller bearing 14 is further supported on a central, radially inwardly directed projection 12d of the central portion 12a and in this way holds the turbine wheel 8 to be rotatable at the housing 12. This central projection 12d restricts, by the way, the receiving chamber 13 for the turbine 7 in the axial direction and simultaneously separates it from an axially connected gear chamber 15.

According to the invention, the above-mentioned reduction gear 10 is in the form of a coaxial gear set, especially a planetary gear or a so-called "harmonic drive" with high reduction and thus in the form of a self-locking gear set. This gear set 10 is accommodated in the gear chamber 15 which is likewise enclosed by the central portion 12a of the housing 12 of the rotary member 4.

In the present embodiment according to FIG. 2 the tubular shank 9 fixedly connected to the turbine 7 consequently forms, at its axially free end, a wheel carrier 9a for the pressure wheels 16 of the so-called harmonic drive 10. The basic principle of this harmonic drive 10 is sufficiently known from prior art and therefore it will be described only generally by way of the enclosed FIG. 3.

Figure 3:
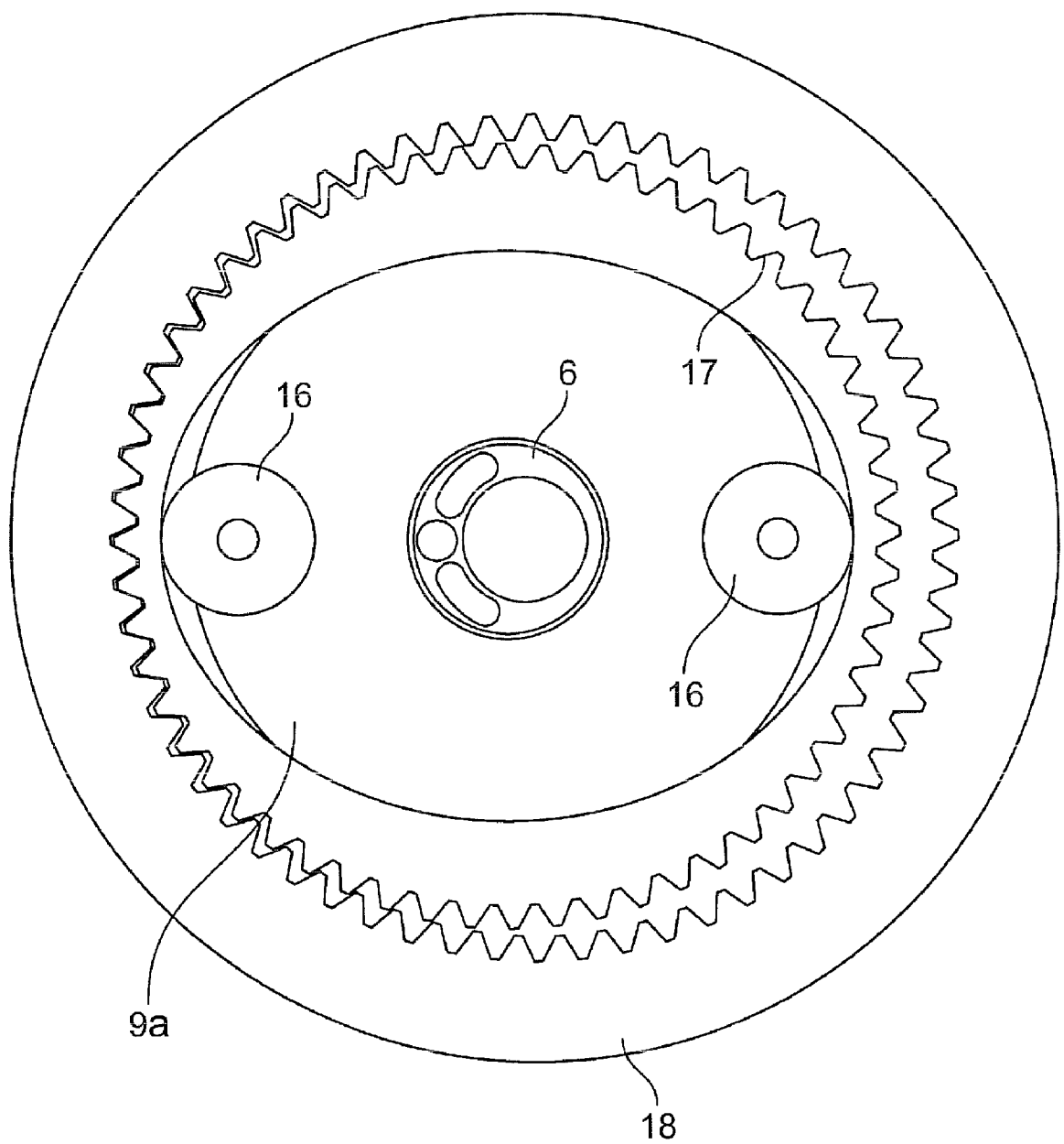
FIG. 3 shows the general layout of a so-called harmonic drive.

According to FIG. 3, such harmonic drive 10 substantially consists of the afore-mentioned wheel carrier 9a on which at least two pressure wheels 16 are supported. Said pressure wheels 16 are arranged eccentrically with respect to the axis of rotation of the wheel carrier 9a and are in mesh with the inside of an outer gearwheel 17 which is likewise appropriately aligned eccentrically with respect to the wheel carrier 9a. The outer gearwheel 17 is in turn in mesh with a fixed ring gear 18 such that during rotation of the wheel carrier 9a an eccentric movement of the outer gearwheel 17 starts whereby the outer gearwheel 17 is forced into a rotation strongly reduced with respect to the rotation of the wheel carrier 9a due to the gear mesh with the ring gear 18. A similar principle of reduction is known, by the way, also in so-called cycloid gear sets so that the above-described harmonic drive 10 could be replaced with a cycloid gear set known per se.

It is also possible to provide a simple planetary gear set. In such an alternative embodiment that is not shown in detail the afore-described tubular shank 9 consequently forms, at its free end, a sun wheel which is operatively engaged with a number of planet wheels. In such case a planetary carrier is preferably fixedly connected to a driven shaft of the gear set which extends axially in the direction of the deflecting 2. The planet wheels are in turn in operative engagement with a ring gear which is preferably formed by the central portion 12a of the housing 12 of the rotary member 4.

As one can further take from FIGS. 1 and 2, in the annular gap between the outer wall 5 and the inner pipe 6 in the area of the endoscope shaft 1 at least two preferably diametrally opposed passages 19 are arranged which open at the transitional area between the endoscope shaft 1 and the rotary member 4 into the turbine receiving chamber 13. The one passage forms an inlet and the other passage forms an outlet for a fluid driving the turbine wheel 8.

At its front facing the axially connected deflecting 2 the outer gearwheel 17 of the reduction gear 10 forms the one driven shaft 11 surrounding the inner pipe 6. The driven shaft 11 is shaped in a kind of pipe frustum on the radial outside of which the deflecting is mounted, for instance, by gluing or by vulcanizing.

Said deflecting 2 substantially consists of a preferably cylindrical outer wall 2a which is provided quasi as an extension of the cylindrical outer wall 5 of the endoscope shaft 1 and, respectively, of the central portion 12a of the rotary member 4. Radially inside said outer wall 2a, i.e. in the annular gap between the inner pipe 6 also passing through the deflecting 2 and the outer wall 2a of the deflecting 2 there is provided a bellows 20 preferably having a pitch circle cross-section which is fastened in the deflecting 2 such that it moves on an orbit along with the driven shaft of the reduction gear about the longitudinal axis of the endoscope shaft 1.

According to the enclosed FIG. 1, in the inner pipe 6 shown there a radially extending orifice 21 is provided through which a pressure medium can be applied to the bellows 20. To put it more concretely, inside or at the inner pipe 6 a pressure pipe (not shown in detail) is provided which opens in the radial direction into a ring chamber 22 formed inside the pipe frustum 11 which constitutes the driven shaft. Thus, during rotation of the driven shaft II the ring chamber 22 rotates as well, wherein a permanent fluid connection with the pressure pipe is maintained due to the radial orifice 21 thereof. The ring chamber 22 in turn is in fluid connection with the bellows 20.

Upon application of pressure the bellows 20 expands due to its structural design preferably in the axial direction of the endoscope shaft 1, whereby the deflecting 2 performs a bending movement in one plane by virtue of the one-sided (eccentric) arrangement of the bellows 20 with respect to the central axis of the endoscope shaft 1. As soon as the pressure medium is deflated from the bellows 20, the latter contracts again, seen in the longitudinal direction, whereby the deflecting adopts its original position again or bends even further in the opposite direction.

Figure 4:
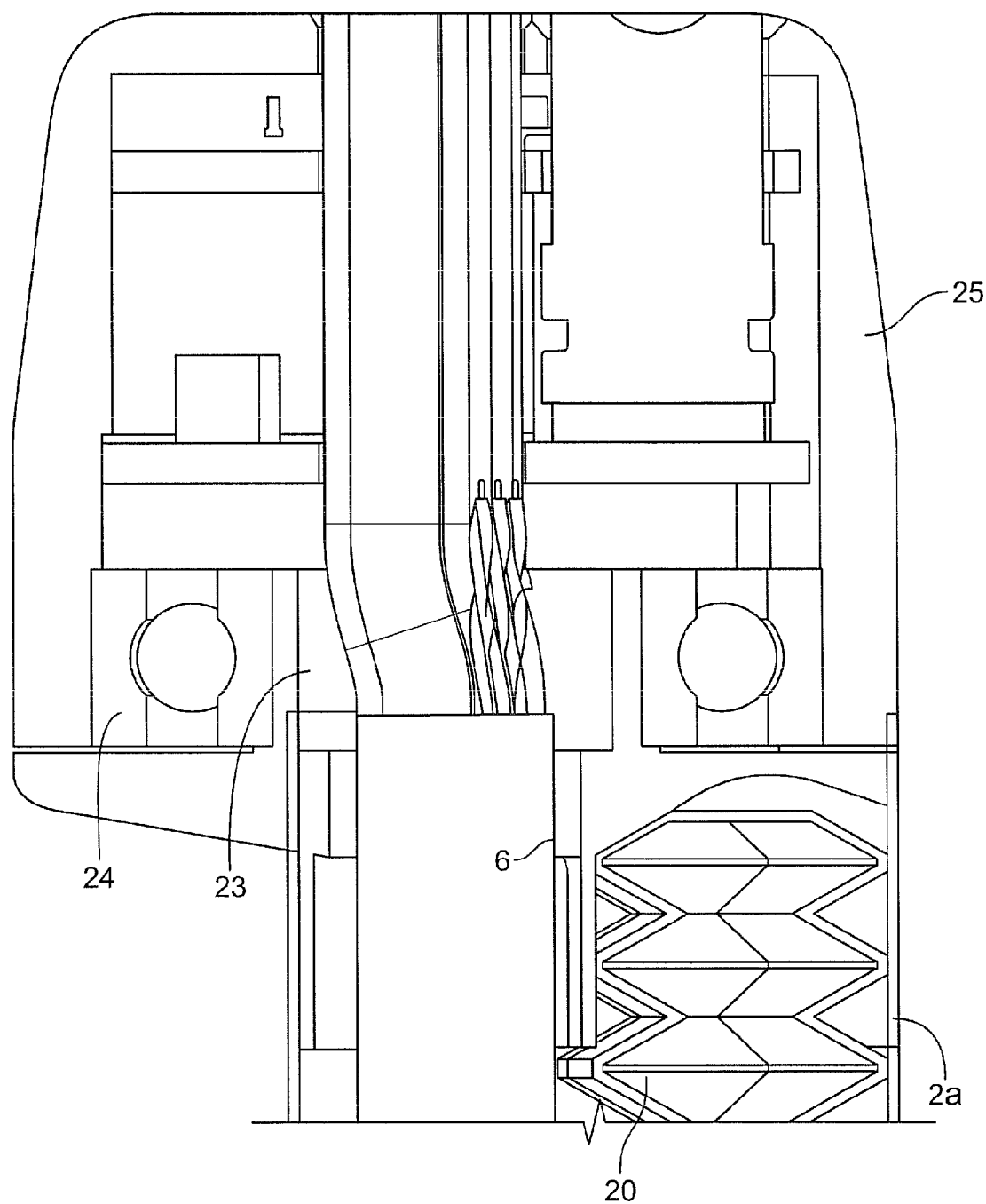
FIG. 4 shows the schematic side view of an endoscope shaft.

In FIG. 4 the endoscope head 3 of the endoscope according to the invention is schematically represented in a side view. It consists, inter alia, of an inner tubular stator 23 that is connected to the inner pipe 6 in a sealing manner. A roller bearing 24 rotatably supporting on the stator 23 a cap 25 which forms a type of cup-shaped housing of the endoscope head 3 is placed onto the stator 23. Inside the cap 25 a plurality of endoscope-specific means such as lighting, optical means, spraying system and the like which are represented only schematically in FIG. 4 are fixed on the same. The stator 23 is open at the front of the cap 25 so that medical instruments can be pushed out of the endoscope through the same.

Hereinafter the functioning of the above-described endoscope according to the invention in accordance with the preferred embodiment shall be illustrated.

The inlet and outlet passages 19 schematically shown in FIG. 2 for the drive of the turbine 8 are preferably connected to a pressure source (not represented) at the proximal end of the endoscope shaft 1. The same also applies to the pressure fluid passage not shown in detail provided inside of or at the inner pipe 6 for operating the bellows 20 which passage is likewise connected to a separate pressure source for operating the deflecting 2. Although both pressure sources are not shown in the enclosed FIG. 1 or 2, they can consist of a manually operated hand pump or an electric pump, however.

As briefly described in the beginning, it is advantageous when inserting the endoscope into a duct-shaped cavity, for instance the intestines of a patient, to dynamically adapt the distal end portion of the endoscope corresponding to the intestinal loops to be passed by forcing the deflecting 2 to perform appropriate bending movements. For this purpose, fluid is optionally pressed into the bellows 20 of the deflecting 2, whereby an appropriate bending movement of the deflecting 2 is caused. However, since preferably only one single bellows 20 is arranged out of center with respect to the central line of the endoscope shaft 1, a bending movement is possible in one plane only (two-dimensional).

In order to compensate that, the rotary member 4 according to the invention is additionally provided.

If a bending of the deflection 2 into different directions (three-dimensional) is necessary, a drive fluid is introduced through the inlet passage 19 to the receiving chamber 13 of the turbine 7 at a predetermined flow rate, whereby the turbine wheel 8 is driven at a corresponding speed. This movement of rotation is transmitted via the tubular shank 9 representing a rotor and the reduction gear 10 arranged downstream thereof with an appropriate reduction to the driven shaft 11 of the reduction gear 10 by which the deflecting 2 and thus also the bellows 20 are fixed. In this way, the deflecting 2 is rotated about the longitudinal axis of the latter.

Due to the fact that the inner pipe 6 of the endoscope shaft 1, which is extended beyond the endoscope shaft 1 and thus passes through the rotary member 4 and the axially connected deflecting 2, is decoupled in terms of rotation and thus remains torque-proof with respect to the rotary member 4 and the deflecting 2, in this way all working and supply passages as well as leads contained therein, as indicated in FIG. 3, can be laid without any rotation compensating elements.

Finally, it is referred to the fact that the above-described embodiment may be further varied in different ways without the design according to the invention described in the beginning being changed. It is possible, for instance, to vary the speed and possibly even the direction of rotation by possibilities for adjustments at the turbine wheel 8.

The bellows 20 has been described in the foregoing as being in the form of a pitch circle in cross-section. It could as well be a normally designed cylindrical bellows.

The invention claimed is:

1. An endoscope comprising:
an endoscope shaft having a distal end and a proximal end;
a rotary member coupled to the distal end of the endoscope shaft;
a bendable operating member coupled to the rotary member opposite the distal end of the endoscope shaft; and
an endoscope head coupled by the bendable operating member to the endoscope shaft to form a tubular component, wherein the rotary member is to rotate the bendable operating member about a longitudinal axis of the endoscope shaft, wherein the bendable operating member has a bending mechanism that permits bending of the endoscope head in only one plane of curvature, wherein the rotary member further comprises a reduction gear.

2. An endoscope according to claim 1, wherein the rotary member further comprises a coaxial drive.

3. An endoscope according to claim 1, wherein the bendable operating member is axially offset with respect to the rotary member.

4. An endoscope comprising:
an endoscope shaft having a distal end and a proximal end;
a rotary member coupled to the distal end of the endoscope shaft;
a bendable operating member coupled to the rotary member opposite the distal end of the endoscope shaft; and
an endoscope head coupled by the bendable operating member to the endoscope shaft to form a tubular component, wherein the bendable operating member bends in substantially only a one plane of curvature, wherein the rotary member is to rotate the bendable operating member about a longitudinal axis of the endoscope shaft, and wherein the rotary member comprises a turbine drive including a turbine wheel that is seated on a rotor and a stator which forms a receiving chamber for the turbine wheel.

5. An endoscope according to claim 4, wherein the rotor is operatively connected to a reduction gear that transmits rotation of the turbine wheel at a predetermined reduction ratio to the bendable operating member.

6. An endoscope according to claim 5, wherein the reduction gear is a self-locking gear set of axial design.

7. An endoscope according to claim 5, wherein the stator forms an outer wall of the rotary member that surrounds the turbine wheel, the rotor and the connected reduction gear form an axial extension of the endoscope shaft.

8. An endoscope according to claim 7, wherein the outer wall forms a guide or a centering for the reduction gear and a ring gear of the reduction gear that is in the form of a planetary gear set.

9. An endoscope according to claim 4, wherein an inlet passage and an outlet passage in the endoscope shaft are to apply a pressure medium to the turbine drive.

10. An endoscope according to claim 7, wherein the outer wall forms a guide or a centering for the reduction gear and a ring gear of the reduction gear that is in the form of a harmonic drive.

11. An endoscope according to claim 5, wherein the reduction gear is a self-locking gear set of axial design further comprising a planetary gear set.

12. An endoscope according to claim 5, wherein the reduction gear is a self-locking gear set of axial design further comprising a harmonic drive.

13. An endoscope according to claim 5, wherein the stator forms an outer wall of the rotary member that surrounds the turbine wheel, wherein the rotor and the connected reduction gear form an axial extension of the endoscope shaft.

14. An endoscope according to claim 13, wherein the outer wall forms a guide or a centering for the reduction gear and a ring gear of the reduction gear that is in the form of a planetary gear set.

15. An endoscope according to claim 5, wherein an inlet passage and an outlet passage in the endoscope shaft are to apply a pressure medium to the turbine drive.

16. An endoscope according to claim 6, wherein an inlet passage and an outlet passage in the endoscope shaft are to apply a pressure medium to the turbine drive.

17. An endoscope comprising:
an endoscope shaft having a distal end and a proximal end;
a rotary member comprising a coaxial drive and coupled to the distal end of the endoscope shaft;
a bendable operating member coupled to the rotary member opposite the distal end of the endoscope shaft; and
an endoscope head coupled by the bendable operating member to the endoscope shaft to form a tubular component, wherein the rotary member is to rotate the bendable operating member about a longitudinal axis of the endoscope shaft, wherein the bendable operating member has a bending mechanism that permits bending of the endoscope head in only one plane of curvature wherein the rotary member comprises a turbine drive including a turbine wheel which is seated on a rotor and a stator that forms a receiving chamber for the turbine wheel.

18. An endoscope according to claim 17, wherein the rotor is operatively connected to a reduction gear that is to transmit rotation of the turbine wheel at a predetermined reduction ratio to the bendable operating member.

19. An endoscope according to claim 17, wherein the turbine wheel and a transmission are axially spaced along a central axis of the endoscope.

20. An endoscope according to claim 18, wherein the turbine wheel and the reduction gear are axially spaced along a central axis of the endoscope.

21. An endoscope comprising:
an endoscope head;
an endoscope shaft having a first central axis and coupled to the endoscope head by a bendable operating member having a second central axis, wherein the first central axis and the second central axis coincide; and
a rotary member disposed between the endoscope shaft and the bendable operating member and configured to rotate the bendable operating member about the first central axis of the endoscope shaft, wherein the rotary member further comprises a reduction gear, and wherein the bendable operating member includes a bellows arranged to one side of the first central axis and/or the second central axis, wherein when the bellows is to expand in an axial direction, the bendable operating member is to bend in one plane of curvature.

* * * * *